United States Patent [19]

Bridge

[11] Patent Number: 5,464,011
[45] Date of Patent: Nov. 7, 1995

[54] TRACHEOSTOMY TUBE

[76] Inventor: Robert S. Bridge, 25 E. LaMar Rd., Phoenix, Ariz. 85012

[21] Appl. No.: 327,617

[22] Filed: Oct. 24, 1994

[51] Int. Cl.$^6$ ................................................. A61M 16/00
[52] U.S. Cl. .............................. 128/207.14; 128/200.26
[58] Field of Search ........................ 128/207.14, 200.26, 128/207.17, 911, 912, DIG. 26, 207.15, 200.24

[56] References Cited

U.S. PATENT DOCUMENTS

| | | | |
|---|---|---|---|
| 3,137,299 | 6/1964 | Tabor . | |
| 3,263,684 | 8/1966 | Bolton . | |
| 4,269,184 | 5/1981 | Montgomery | 128/207.14 |
| 4,877,025 | 10/1989 | Hanson | 128/207.16 |
| 5,048,518 | 9/1991 | Eliachar et al. | 128/207.14 |
| 5,064,417 | 11/1991 | Andreussi | 604/175 |
| 5,092,850 | 3/1992 | Buma | 604/175 |
| 5,287,852 | 2/1994 | Arkinstall | 128/207.14 |

*Primary Examiner*—Edgar S. Burr
*Assistant Examiner*—V. Srivastaya
*Attorney, Agent, or Firm*—Kinney & Lange

[57] ABSTRACT

The tracheostomy tube includes an elongate inner tube, an elongate insert, and an outer tube. The inner tube has a side wall with an outer surface having threads and a distal end of the inner tube defines an annular collar. The inner tube has a longitudinal slot extending through the side wall and the collar from the distal end to a proximal end of the inner tube. The insert is slidably mountable in the slot of the inner tube and collar. The outer tube has an inner surface with grooves formed therein to threadingly engage the threads of the inner tube to secure the tracheostomy tube to a neck of a patient.

20 Claims, 7 Drawing Sheets

TRACHEOSTOMY TUBE

BACKGROUND OF THE INVENTION

The present invention relates to tubes insertable within the human body. In particular, the present invention relates to a tracheostomy tube for insertion within a neck of a patient.

Tracheostomy tubes have been used for many years to provide an airway in a patient with specific respiratory difficulties. The tracheostomy tube provides access to the trachea below the larynx in the neck of a patient. The primary objective in using a tracheostomy tube is to provide adequate airway ventilation. The tube can permit passive ventilation, i.e., ventilation occurring without assistance. Alternatively, the tracheostomy tube can provide access for mechanically assisted ventilation for patients that are unable to breath on their own.

Conventional tracheostomy tubes are relatively long and are formed in the shape of a gradual curve such that opposite ends of the tube are disposed at a large angle (e.g., 90°) relative to one another. The conventional tracheostomy tube is generally made of hard plastic and can include an expandable and collapsible cuff disposed at the inserted distal end of the tube. The expandable cuff, when expanded, acts to secure an inserted distal end of the tube within the trachea. A proximal end of the tube is typically secured to the exterior surface of the neck with a bracket wherein an elastic band or tie is fastened to the bracket and extends around the neck of the patient to anchor the bracket and proximal end of the tube relative to the trachea. This method of securing the tracheostomy tube results in a relatively loose fit of the tube within the trachea. Amongst other difficulties, this loose fit makes it difficult to obtain adequate air pressure when providing mechanically assisted ventilation through the tracheostomy tube.

In addition, conventional tracheostomy tubes are undesirable to use because they typically include an inflation tube or other inflation means which must extend from the expandable cuff to the proximal end of the tracheostomy tube to provide for inflation of the cuff. This typically results in the inflation tube extending outwardly from the exterior surface of the neck creating an unsightly appearance. Moreover, conventional tracheostomy tubes are designed such that the proximal end of the tube extends outwardly from a bracket mounted on the neck of the patient, which further contributes to the unsightly appearance of the tracheostomy tube within the neck of the patient. In addition, conventional tracheostomy tubes are designed to allow insertion of a cannula through the tracheostomy tube wherein a proximal end of the cannula locks to the proximal end of the tube. This design results in a proximal end of the cannula extending even further outwardly from the bracket than the proximal end of the tube. Obviously, this further contributes to the unsightly appearance of conventional tracheostomy tubes.

Conventional tracheostomy tubes have a continuous side wall made of hard plastic which is relatively inflexible and which tends to make insertion of the tracheostomy tube difficult. Insertion of the conventional tracheostomy tube typically requires an obturator insertable through the tracheostomy tube to temporarily provide a rounded tip portion at the distal end of the tracheostomy tube during insertion of the tube through the stoma and into the interior of the tracheal lumen.

Conventional tracheostomy tubes also complicate the patient's breathing because of the relatively long portion of the tracheostomy tube which extends down into the trachea. This long tube makes breathing more difficult as well as complicating or hampering the ability of a patient to expel excess mucous by the coughing reflex.

Finally, several sizes of conventional tracheostomy tubes must be available on demand to accommodate different sized tracheal stomas. This requires shelf storage of several different size tracheostomy tubes increasing inventory costs and resulting in tubes which exceed their sterility limit for shelf storage.

Various attempts have been made to improve upon the conventional tracheostomy tube. For example, U.S. Pat. Nos. 3,263,684, 3,137,299, and 5,287,852 all provide examples of relatively straight non-conventional tracheostomy tubes designed to avoid a tracheostomy tube having a long portion extending downwardly into the lumen of the trachea. This relatively straight tube design avoids significant contact between the distal end of the tracheostomy tube and the mucous lining on the tracheal wall. This aids in preventing infection of the trachea and bronchial tree as well as avoiding damage to the cilia which acts to move excess mucous upward through the trachea for eventual expulsion through the tracheostomy tube or the mouth.

These non-conventional tracheostomy tubes still have several features which detract from their performance and general desirability of use. These non-conventional tracheostomy tubes each include a significant portion of the tube that extends outwardly from the neck of the patient creating a rather unsightly and noticeable cosmetic appearance bringing unwanted attention to the patient by curious observers. Moreover, although these non-conventional tracheostomy tubes avoid some of the disadvantages of the conventional tracheostomy tubes, these non-conventional tracheostomy tubes have not been widely accepted in the marketplace. This could result from their unsightly cosmetic appearance or from other functional considerations. One functional consideration is how well the tracheostomy tube is secured within the stoma through the neck of the patient into the trachea. The Tabor U.S. Pat. No. 3,137,299 and Bolton U.S. Pat. No. 3,263,684 each disclose non-conventional tracheostomy tubes which require the use of an elastic band or cord to pass around the patient's neck for securing the tracheostomy tube relative to the trachea and neck. It is desirable to avoid the use of this securing band or cord which brings unwanted attention to the patient and which can be uncomfortable or bothersome for the patient to wear. Another functional consideration includes ease of insertion and removability of the tracheostomy tube through the stoma and into the trachea. Although some of the non-conventional tracheostomy tubes are made of materials which may be resilient, these non-conventional tracheostomy tubes fail to include design features that significantly aid in the insertion and removal of the tracheostomy tube within the stoma. Moreover, even the resilient tubes, which may facilitate insertion somewhat, can be less desirable once seated within the stoma because the resilience of the materials may cause the tracheostomy tube to be less stable relative to the trachea.

In addition, the relatively straight tube design can make it more difficult to pass accessory devices through the tracheostomy tube down into the trachea. The straightness of the tube tends to direct any accessory device inserted therein into the posterior wall of the trachea opposite the location of the tube within the anterior wall of the trachea.

Accordingly, tracheostomy tubes of the prior art have many limitations. First, conventional tracheostomy tubes having a long tubular portion which extends down into the trachea tending to obstruct the lumen of the trachea as well as potentially damaging the cilia and bronchial tree. These conventional tracheostomy tubes also typically fit loosely within a tracheal stoma and require an extra elastic band to pass around the neck of the patient to secure the tracheostomy tube relative to the trachea. A proximal end of the conventional tracheostomy tubes also typically protrude outwardly from the skin surface of the neck and along with the elastic band placed around the neck of the patient, create an unsightly appearance attracting unwanted attention from curious observers. The securing band can be uncomfortable.

Even non-conventional tracheostomy tubes (relatively straight tubes) have many limitations. Like the conventional tracheostomy tubes, the relatively straight tubes also protrude outwardly from the skin surface of the neck and some require elastic bands to be placed around the neck, thus still creating an unsightly appearance for the patient. The relatively straight tracheostomy tubes make it more difficult to insert cannulas and other accessory devices through the tracheostomy tube because no means are provided for guiding the accessory device or cannula downward into the trachea. Therefore, the non-conventional relatively straight tracheostomy tube tends to cause accessory devices in cannulas to contact the posterior wall of the trachea upon insertion. Finally, although some conventional tracheostomy tubes as well as non-conventional tracheostomy tubes are resilient, insertion and removal of these prior art tracheostomy tubes is still difficult to achieve when inserting a tracheostomy tube that is properly sized to result in a snug fit within a tracheal stoma. Last, both conventional and non-conventional tracheostomy tubes of the prior art require a full range of sizes be kept in inventory so the proper sized tracheostomy tube is available for any given tracheal stoma.

SUMMARY OF THE INVENTION

The present invention provides convenient and unobstructed access to the trachea below the larynx in the neck of a patient.

A tracheostomy tube of the present invention includes an inner tube insertable through a tracheal stoma in the neck of a patient and having a collar at a distal end of the inner tube for anchoring against an inner surface of an anterior wall of the trachea. The inner tube has a longitudinal slot in the side wall of the inner tube and collar permitting the inner tube to be compressed radially inward to facilitate insertion of the tube within the tracheal stoma. An elongate insert is slidably mountable in the slot of the inner tube to yield a substantially continuous side wall for the combination of the inner tube and insert. An elongate outer tube is adapted to threadingly engage a proximal end of the inner tube. The outer sleeve includes a flange at a distal end of the outer tube for anchoring against an outer surface of the anterior wall of the trachea. The inner tube and outer tube can be urged together by threaded engagement to anchor the collar of the inner tube and the flange of the outer tube against the anterior wall of the trachea. This combination of the outer tube and inner tube securely fasten the tracheostomy tube of the present invention relative to the trachea.

The collar at the distal end of the inner tube preferably has a spherically curved shape for reciprocally engaging an inner surface of the anterior wall of the trachea to facilitate secure anchoring of the inner tube relative to the trachea. The flange at the first end of the outer tube also preferably has a spherically curved shape for reciprocally engaging an outer surface of the anterior wall of the trachea to facilitate secure engagement of the outer tube relative to the trachea. In addition, both the first end of the inner tube and the outer tube preferably are beveled such that a length of a top portion of the inner and outer tube, respectively, is less than a length of the bottom portion of the inner and outer tube, respectively, to further facilitate reciprocal engagement of the inner tube and outer tube with the anterior wall of the trachea.

The tracheostomy tube of the present invention provides several important advantages. First, the combination of the inner tube and outer tube yield a tracheostomy tube which has a very low profile, i.e., extends outwardly from the neck surface for a minimal distance so that the end of the tracheostomy tube is relatively flush with the neck surface. Accordingly, when a tracheostomy button is placed over the proximal end of the outer tube, the tracheostomy tube is hardly noticeable and does not attract unwanted attention. This low profile is achieved since the outer tube is threadingly secured to the inner tube below the skin surface of the neck. Second, the tracheostomy tube of the present invention is extremely stable relative to the trachea. This facilitates mechanically assisted ventilation as well as insertion of other accessory devices within the tracheostomy tube. The secure attachment of the tracheostomy tube to the trachea is achieved by a combination of the collar on the distal end of the inner tube which rests against the inner surface of the anterior wall of the trachea and the flange at the distal end of the outer tube, which rests against the outer surface of the anterior wall of the trachea. The flange of the outer tube is urged toward the collar of the inner tube by moving the outer tube longitudinally relative to and toward the distal end of the inner tube to cause the anterior wall of the trachea to be sandwiched between the flange of the outer tube and the collar of the inner tube. This yields a tracheostomy tube that is securely fastened and stable relative to the trachea without the need for accessory fastening device such as an elastic band or cord to be secured about the neck of a patient. Of course, the lack of an additional securing means, such as a neck band, further creates a cosmetic appearance that is unlikely to attract unwanted attention from curious observers. The lack of an additional securing means is also more comfortable for the patient since no band extends around the patient's neck.

The tracheostomy tube of the present invention is also particularly convenient to insert and remove relative to the trachea. The inner tube of the tracheostomy tube includes a slot that extends longitudinally along the entire length of the inner tube to facilitate radially compressing the inner tube to temporarily reduce its outer diameter. This effectively reduced outer diameter facilitates insertion and removal of the inner tube through the stoma in the neck of the patient and through the anterior wall of the trachea. The slot design of the inner tube allows the use of a plastic material for the inner tube which is typically harder and stiffer than the resilient materials used in some nonconventional prior art tracheostomy tubes. This harder plastic material construction increases the stability of the tube when fastened relative to the trachea. The slot design of the inner tube also allows a single sized inner tube to be adaptable to fit different sized stomas within the neck of a patient. The slot of the inner tube slidably receives an elongate insert of a selected predetermined width to achieve the desired inner and outer diameter of the inner tube and insert combination. This slot design of the inner tube permits a physician to insert the inner tube into the anterior wall of the trachea and then mount different sized elongate inserts into the slot of the inner tube to achieve the best fit of the inner tube within the stoma in the neck of the patient. This eliminates guesswork when choosing the appropriate size tracheostomy tube for insertion within the stoma and trachea.

The tracheostomy tube of the present invention also can be modified so that the combination of the inner tube and insert are formed with an inner diameter, while remaining relatively uniform and constant, that has a downward taper at the distal end. This taper provides a general gentle downward curve of the tracheostomy tube adjacent the anterior wall of the trachea to facilitate insertion and removal of accessory devices such as inner cannulas and other insertable devices. The downward taper minimizes the likelihood of one of the accessory devices entering the tracheostomy tube and then being forced into the posterior wall of the trachea. Instead, the inserted devices are guided downwardly by the tapered distal end of the tracheostomy tube of the present invention into the lumen of the trachea avoiding direct contact with the posterior wall of the trachea.

The tracheostomy tube of the present invention is easily insertable and removable within the neck of a patient and is securely fastenable to a trachea while maintaining a low profile on the skin surface of the neck. A single size inner tube of the tracheostomy tube can accommodate different sized tracheal stomas thereby reducing inventory costs due to excess supply and sterility expiration from long duration storage.

While the above-described figures illustrate various embodiments of the present invention, it should be understood that the figures illustrate the present invention by representation and not by limitation. For example, in some instances, the drawings have been enlarged for clarity and thus are not necessarily to scale. In addition, throughout the specification of the application, various terms are used such as "left", "right", "top", "bottom", "side", and the like. These terms denote directions with respect to the drawings and are not limitations of orientation of the present invention. Rather, these terms are provided for clarity in describing the relationships between components of the tracheostomy tube and between the tracheostomy tube and a trachea of a patient.

DETAILED DESCRIPTION OF THE PREFERRED EMBODIMENTS

Figure 1:
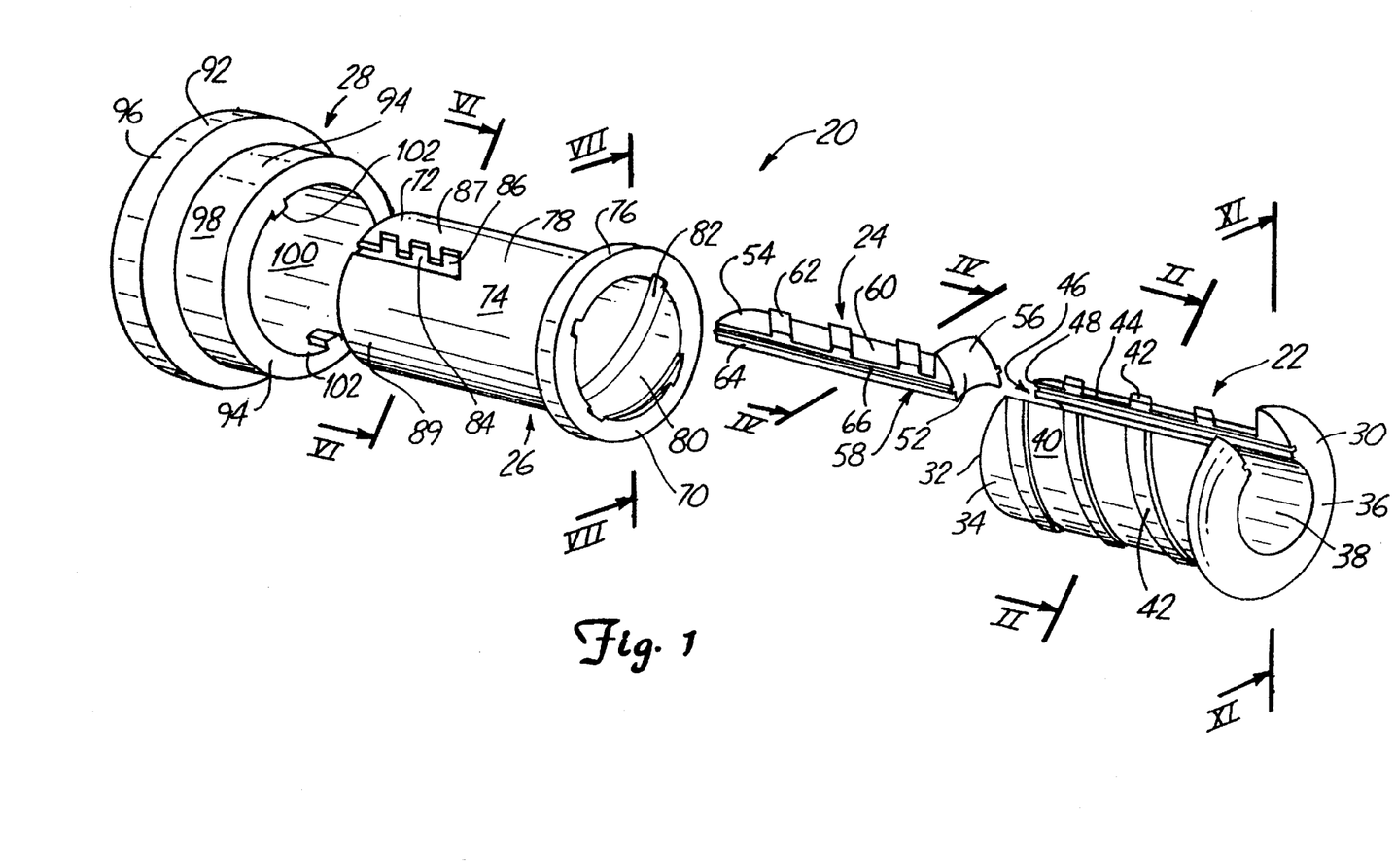
FIG. 1 is an exploded perspective view of a tracheostomy tube of the present invention.
Figure 2:
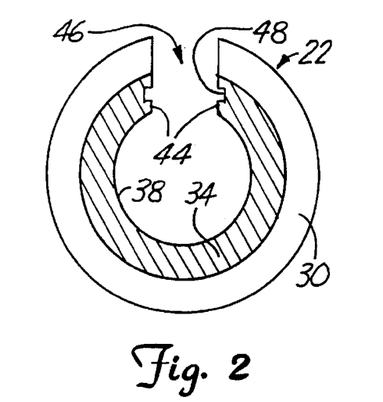
FIG. 2 is a view in section of the inner tube of FIG. 1 as taken along the lines 2—2.
Figures 3, 4:
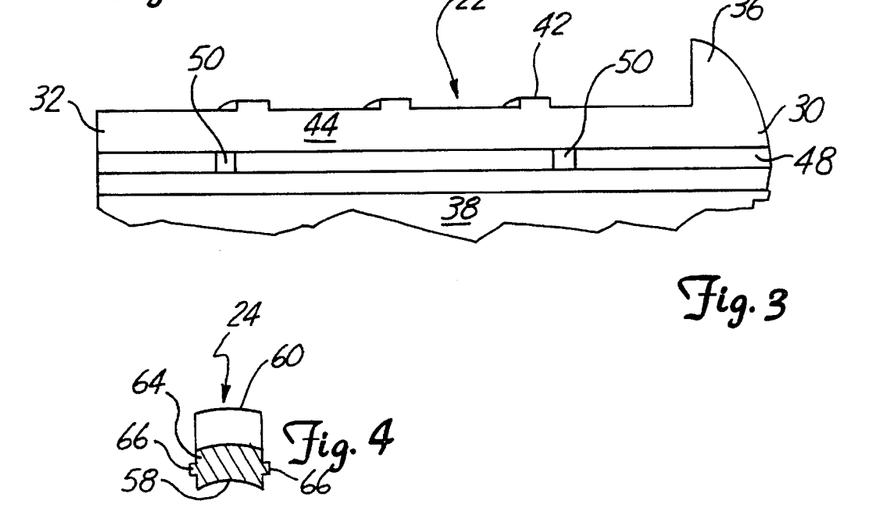
FIG. 3 is an enlarged view in elevation of an edge of a side wall of an inner tube of the present invention of FIG. 1.
FIG. 4 is a view in section of the insert of FIG. 1 as taken along lines 4—4.

A tracheostomy tube of the present invention is illustrated generally in FIG. 1 at 20. The tracheostomy tube 20 includes an inner tube 22, an insert 24, an outer tube 26, and a button 28. The elongate flexible inner tube 22 has a distal end 30 and a proximal end 32 and is defined by a side wall 34 which extends between the distal end 30 and the proximal end 32. A collar 36 is fixed to the distal end 30 of the inner tube 22. The inner tube 22 has an inner surface 38 and an outer surface 40 with threads 42 formed thereon. The side wall 34 has a pair of opposed side edges 44 which define a slot 46 extending from the distal end 30 to the proximal end 32 of the inner tube 22. The opposed side edges 44 each include a groove 48 formed therein which extends from the distal end 30 to the proximal end 32 of the inner tube 22. FIG. 2 provides an enhanced illustration of the slot 46 and grooves 48 formed in the side edges 44 of the inner tube 22. As shown in FIG. 3, each groove 48 has at least one recess 50 formed therein.

Figure 5:
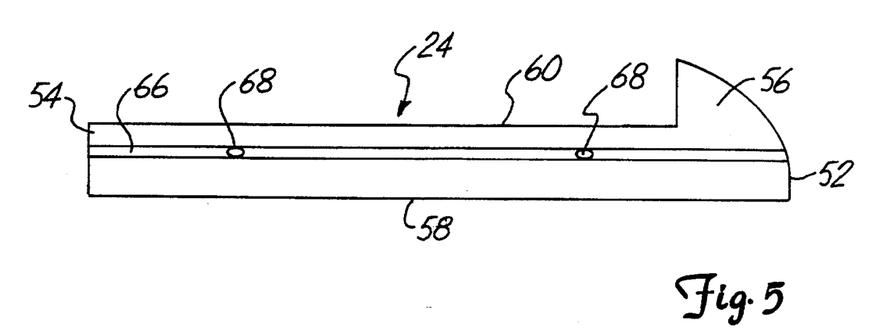
FIG. 5 is an enlarged side view in elevation of a side edge of an insert of the present invention of FIG. 1.

The insert 24, as shown in FIG. 1, has a distal end 52 and a proximal end 54, and includes a collar portion 56 fixed to the distal end 52 of the insert 24. The insert 24 has an inner surface 58 and an outer surface 60 with threads 62 formed thereon. The insert 24 also has a pair of oppositely disposed side edges 64 wherein each side edge 64 has an elongate ridge 66 formed thereon. FIG. 4 provides an enhanced illustration of ridges 66 on side edges 64 of the insert 24. As shown in FIG. 5, each ridge 66 has at least one knob 68 formed thereon.

The elongate outer tube 26, as shown in FIG. 1, has a distal end 70 and a proximal end 72 with a side wall 74 extending between the distal end 70 and the proximal end 72. A flange 76 is fixed to the distal end 70 of the outer tube 26. The outer tube 26 has an outer surface 78 and an inner surface 80 with grooves 82 formed therein. A pair of elongate locking grooves 84 are formed in the outer surface 78 of the side wall 74 at the proximal end 72 of the outer tube 26 in both a top portion 87 and a bottom portion 89 (see FIG. 6) of the outer tube 26. Each locking groove 84 includes at least one side channel 86. FIG. 7 further illustrates the outer tube 26, particularly the grooves 82 formed on the inner surface 80 of the side wall 74.

The button 28, as shown in FIG. 1, has a distal end 90 and a proximal end 92. The button 28 includes an inner tubular portion 94 and an outer disc portion 96. The inner tubular portion 94 has an outer surface 98 and an inner surface 100 with a pair of oppositely disposed pins 102 formed on the inner surface 100 at the distal end 90 of the button 28.

The inner tube 22 is preferably made of a hard plastic material (e.g., polyvinyl chloride) that is relatively flexible. Accordingly, the presence of the slot 46 in the inner tube 22 permits the inner tube 22 to be radially compressed so that an outer surface 40 of the inner tube 22 temporarily has an effective outer diameter less than an original outer diameter of the outer surface 40. Radial compression can be applied by applying finger pressure on opposite sides of the inner tube 22 and squeezing the inner tube 22 to effectively reduce its outer diameter. Alternatively, the slot 46 of the inner tube 22 permits the inner tube 22 to be radially expanded so that an outer surface 40 of the inner tube 22 temporarily has an effective outer diameter greater than an original outer diameter of the outer surface 40. The material of the inner tube 22 is also made so that the outer surface 40 of the inner tube returns to its original outer diameter once the force causing radial compression or radial expansion is removed from the inner tube 22. Although the inner tube 22 can be made from a plastic material, it can also be made from a hard rubber material. The insert 24 and the outer tube 26 are preferably made of the same material as the inner tube 22.

The insert 24 is slidably mountable within the slot 46 of the inner tube 22. The grooves 48 formed in side edges 44 of the inner tube 22 are sized and adapted to slidingly receive the ridges 66 formed on the side edges 64 of the insert 24 to permit longitudinal sliding movement of the insert 24 relative to the slot 46. The recesses 50 of the grooves 48 are sized and adapted to slidably receive the knobs 68 on the ridges 66 of the insert 24 so that the knobs 68 snap fit within the recesses 50. This snap fit locks the insert 24 into fixed position relative to the inner tube 26. The recesses 50 are aligned and spaced so that once the knobs 68 snap fit within the respective recesses 50, a distal end 52 of the insert 24 will be in substantially flush alignment with a distal end 30 of the inner tube 22 and a proximal end 54 of the insert 24 will be in substantially flush alignment with the proximal end 32 of the inner tube 22. Of course, other means can be employed to prevent longitudinal sliding movement of the insert beyond a distal end of the inner tube. In this locked position, the threads 62 on the outer surface 60 of the insert 24 will align with the threads 42 on the outer surface 40 of the inner tube 22, since the insert 24 has a length substantially equal to the length of the inner tube 22. The insert 24 has a thickness substantially equal to the thickness of the side wall 34 defining the inner tube 22. Accordingly, the inner surface 58 of the insert 24 will be substantially aligned (flush) with the inner surface 38 of the inner tube 22 and the outer surface 60 of the insert 24 will be substantially aligned (flush) with the outer surface 40 of the inner tube 22. This alignment results in a relatively continuous and uniform inner diameter and outer diameter for the inner surface and outer surface, respectively, of combination of the insert 24 and inner tube 22.

The outer tube 26 is rotatably mountable on a combination of the inner tube 22 and the insert 24 mounted therein. The outer tube 26 has an inner surface 80 having an inner diameter substantially equal to the outer diameter of the outer surface 40 of the inner tube 22. The grooves 82 formed in the inner surface 80 of the outer tube 26 are sized and aligned to reciprocally engage the threads 42 formed on the outer surface 40 of the inner tube 22 and the threads 62 on the insert 24 permitting threaded engagement between the outer tube 26 and the combination of the inner tube 22 and the insert 24. This engagement allows longitudinal movement of the outer tube 26 relative to the inner tube 22 as the outer tube 26 rotates about the outer surface 40 of the inner tube 22. Threaded engagement between the inner tube 22 and the outer tube 26 also provides a means for securely fastening the outer tube 26 relative to the inner tube 22 because of the snug fit between the inner tube 22 and outer tube 26.

The button 28 is slidably mountable over the proximal end 72 of the outer tube 26. The oppositely disposed pair of locking grooves 84 of the outer tube 26 are sized and adapted to slidingly receive the oppositely disposed pins 102 of the inner tubular portion 94 of the button 28. The inner surface 100 of the inner tubular portion 94 of the button 28 has an inner diameter substantially equal to the outer diameter of the outer surface 78 of the outer tube 26. Reciprocal engagement of the pins 102 of the button 28 within the locking grooves 84 of the outer tube 26 permits the button 28 to slide longitudinally relative to and over the proximal end 72 of the outer tube 26. The side channels 86 extending from the locking grooves 84 of the outer tube 26 permit the button 28 to be rotated relative to the proximal end 72 of the outer tube 26 such that the pins 102 slidably lock, i.e., twist-lock, within one of the side channels 86 to securely fasten the button 28 to the outer tube 26.

Figure 8:
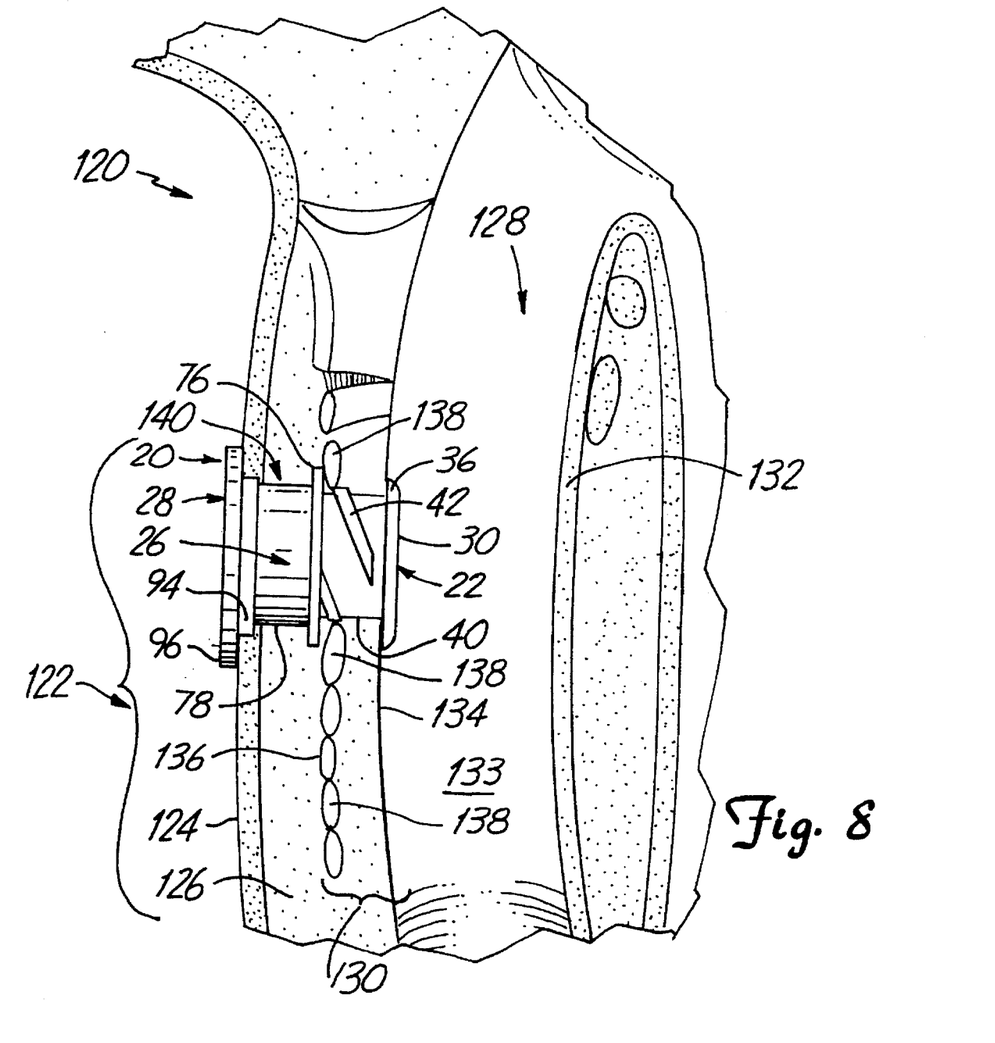
FIG. 8 is a sectional view of a tracheostomy tube of the present invention secured to a trachea within a neck of a patient.

In use, the tracheostomy tube 20 of the present invention is secured to a neck of a patient. FIG. 8 illustrates a neck 120 of a patient including a throat portion 122. The neck 120 includes a skin surface 124, throat tissue 126, and a trachea 128. The trachea 128 includes an anterior wall 130 and a posterior wall 132 with a lumen 133 being defined therebetween. The anterior wall 130 has an inner surface 134 and an outer surface 136. The anterior wall of the trachea 128 is substantially defined by a series of cartilage rings 138. A tracheal stoma 140 extends from the skin surface 124 through the throat tissue 126 and the anterior wall 130 of the trachea 128. The stoma 140 provides an air passageway between the surrounding environment and the lumen 133 of the trachea 128. The stoma 140 has a diameter substantially equal to the outer diameter of the tracheostomy tube 20.

A method of securing the tracheostomy tube 20 to a neck 120 of a patient can include the following steps. First, the stoma 140 must be prepared within the throat portion 122 of the neck 120 of the patient. The stoma 140 is typically made near the upper portion of the trachea 128 so that the stoma 140 has at least one cartilage ring 138 defining an upper boundary of the stoma and at least one cartilage ring 138 defining a lower boundary of the stoma 140. Next, the physician grasps the inner tube 22 and orients the inner tube 22 so that the distal end 30 of the inner tube 22 is aligned to enter the stoma 140. The inner tube 22 is squeezed to radially compress the inner tube 22 to temporarily reduce the outer diameter of the outer surface 40 of the inner tube 22 to an effective outer diameter, which is less than the inner diameter of the stoma 140. The physician then advances the distal end 30 of the inner tube 22 into and through the stoma 140, while still squeezing the inner tube 22, to permit the collar 36 of the inner tube 22 to pass into the lumen 133 of the trachea 128. The inner tube 22 is then further positioned so that the collar 36 of the inner tube 22 seats firmly against the inner surface 134 of the anterior wall 130 of the trachea 128 at which time the physician releases the inner tube 22 allowing the outer surface 40 of the inner tube 22 to return to its original outer diameter. The tendency of the inner tube 22 to return to its original outer diameter causes the outer surface 40 of the inner tube 22 to press against the wall of the stoma 140 thereby further anchoring the inner tube 22 within the stoma 140. In this position, the proximal end 32 of the inner tube 22 extends outwardly from the anterior wall 130 of the trachea 128 and is adjacent to the skin surface 124. The inner tube 22 is oriented so that its slot 46 is aligned vertically substantially parallel to a longitudinal axis of the trachea 128.

As seen in FIG. 8, the threads 42 on the outer surface 40 of the inner tube 22 preferably terminate just short of the collar 36. This spacing (absence of threads) between the end of threads 42 and the collar 36 aids in establishing a firm seal between the outer surface 40 of the inner tube 22 and the anterior wall of the trachea.

Next, the physician grasps the insert 24 by the fingers, or with a tool, and orients the insert 24 relative to the inner tube 22 so that the distal end 52 of the insert 24 is aligned with the slot 46 of the inner tube 22. The physician then advances the distal end 52 of the insert 24 into the slot 46 of the inner tube 22 so that the ridges 66 of the insert 24 slidably engage the grooves 48 of the inner tube 22. The insert 24 is advanced distally through the slot 46 of the inner tube 22 until the knobs 68 on the ridges 66 of the insert 24 snap fit into the recesses 50 of the grooves 48 of the inner tube 22 thereby securely mounting the insert 24 within the slot 46 of the inner tube 22. In this locked position, the threads 62 of the insert 24 are in alignment with the threads 42 of the inner tube 22, and the distal end of the insert 24 is in substantially flush alignment with the distal end 30 of the inner tube 22. In addition, the combination of the insert 24 and the inner tube 22 provide a substantially continuous side wall having an inner surface defining a through passage from the lumen 133 of the trachea 128 to the environment outside the skin surface 124 of the neck 120.

The next step of installing the tracheostomy tube 20 includes orienting the outer tube 26 so that its distal end 70 faces the proximal end 32 of the inner tube 22 resting within the stoma 140. The outer tube 26 is advanced distally toward the inner tube 22 (and insert 24) until the grooves 82 on the inner surface 80 of the outer tube 26 threadingly engage the threads 42 of the inner tube 22 and the threads 62 of the insert 24. Upon threaded engagement, the outer tube 26 is rotated relative to the inner tube 22 and insert 24 to advance the distal end 70 of the outer tube 26 distally toward the distal end 30 of the inner tube 22. The outer tube 26 is advanced distally relative to the inner tube 22 until the flange 76 of the outer tube 26 presses firmly against the outer surface 136 of the anterior wall 130. In this position, the flange 76 of the outer tube 26 and the collar 36 of the inner tube 22 squeeze the anterior wall 130 of the trachea 128, which is sandwiched between the inner tube 22 and outer tube 26. This secures the outer tube 26 relative to the inner tube 22 and secures the tracheostomy tube 20 relative to the anterior wall 130 of the trachea 128. In this position, the proximal end 72 of the outer tube 26 is closely adjacent and in substantial flush alignment with the skin surface 124 of the neck 120.

At this point, the method of inserting the tracheostomy tube of the present invention can be considered complete. However, additional steps can include securing the button 28 onto the proximal end of the outer tube 26, or inserting an accessory device or cannula through the tracheostomy tube 20.

Figure 6:
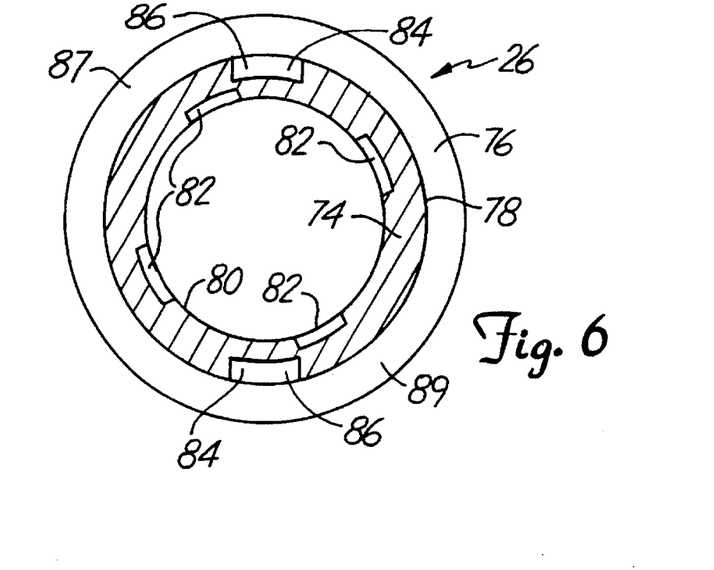
FIG. 6 is a view in section of the outer tube of FIG. 1 as taken along lines 6—6.
Figure 7:
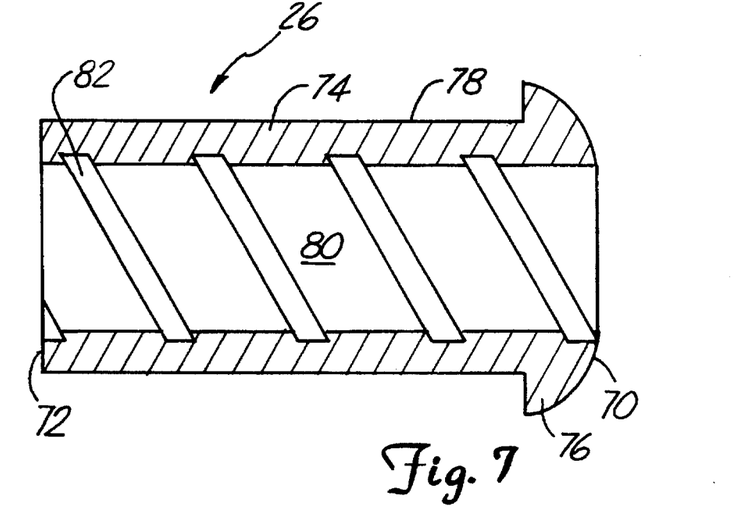
FIG. 7 is a view in section of the outer tube of FIG. 1 as taken along the lines 7—7.

To secure the button 28 on the outer tube 26 as shown in FIG. 6, the distal end 90 of the button 28 is advanced distally toward and aligned with the proximal end 72 of the outer tube 26 such that the pair of oppositely disposed pins 102 of the button 28 slidably engage the oppositely disposed locking grooves 84 of the outer tube 26. The button 28 is slidably advanced distally relative to the outer tube 26 until the outer disc portion 96 of the button 28 firmly contacts the skin surface 124 of the neck 120. The button 28 is then rotated relative to the outer tube 26 such that the pins 102 slidably engage the nearest pair of oppositely disposed side channels 86 (on both the top and bottom of outer tube 26) to prevent longitudinal sliding movement of the button 28 relative to the outer tube 26 thereby locking the button 28 on the proximal end 72 of the outer tube 26.

Once the button 28 has been secured onto the outer tube 26, the button 28 can also be removed to allow an accessory device such as a inner cannula (not shown) to be inserted through the tracheostomy tube 20 into the lumen 133 of the trachea 128. The accessory device such as the cannula preferably would have locking pins similar to pins 102 of the button 28 suitable for slidable locking engagement with the locking grooves 84 of the outer tube 26 to securely fasten the accessory device to the outer tube 26 of the tracheostomy tube 20. An inner cannula provides a lining to the tracheostomy tube 20 so that the tracheostomy tube 20 is maintained free of debris and mucous on its inner surface (inner surface 38 of inner tube 22). Instead, any excess mucous or debris would adhere to the lining provided by the inner cannula. With this arrangement, the inner cannula can be easily removed for cleaning while the tracheostomy tube 20 can remain in place within the stoma 140.

The tracheostomy tube of the present invention also accentuates the use of other accessory devices adapted for insertion through the tracheostomy tube. For example, an accessory tube may include a high pressure inflatable cuff disposed at a distal end of the accessory tube for sealing the distal end of the accessory tube relative to the lumen 133 of the trachea 128. This cuffed accessory tube is used with a mechanical assist ventilator to provide inhalation and exhalation for the patient. Because of the high vacuum pressures created within the trachea during mechanically assisted ventilation, particularly elevated expiratory pressures, it is important to maintain a good seal between the cuff and the lumen of the trachea. Conventional tracheostomy tubes are not adequately secure within the stoma to satisfactorily maintain this seal. In particular, a loose fit of a prior art tracheostomy tube within a tracheal stoma contributes to unwanted movement of the high pressure cuff of the accessory tube relative to the tracheal lumen. This loose fit is commonly caused by an elastic neck band being a main securing component for the prior art tracheostomy tube. This securing method does not prevent unwanted movement of the tracheostomy tube within the stoma during gross physical movements of the patient or during jostling of the ventilator connection to the tracheostomy tube. Accordingly, this unwanted movement caused by the loose fit of the prior art tracheostomy tube diminishes the effectiveness of the seal between the cuff and the tracheal lumen. However, the tracheostomy tube of the present invention facilitates a good seal between the cuff and tracheal lumen because the tracheostomy tube is especially secure within the stoma. This secure and stable tracheostomy tube permits the accessory tube cuff to move with the trachea of the patient.

The inner tube 22 of the tracheostomy tube 20 of the present invention is designed so that a single sized inner tube can be used for any desired size tracheal stoma (within the range of common sized stomas). Although other sizes are possible, the inner tube 22 is preferably provided having an inner diameter of seven-sixteenth inches. The slot 46 is preferably one quarter inch wide and the side wall preferably has a thickness in the range of one eighth inch.

Different sized outer tubes and inserts are provided for use with the inner tube 22 to achieve a tracheostomy tube 20 that fits appropriately within the stoma 140. The insert 24 can be provided in several sizes. For instance, the insert 24 can have a width of one quarter inch so that when inserted in the slot 46 of the inner tube 22, an inner diameter of seven-sixteenth inches is achieved for the combination of the inner tube 22 and insert 24. To create a good fit within a smaller diameter tracheal stoma, the insert 24 can have with a width of three-sixteenth inch so that when inserted within the slot 46 of a slightly radially compressed inner tube 22, an inner diameter of three-eighth inch is achieved for the combination of the insert 24 and inner tube 22. Alternatively, to create a good fit within a larger diameter stoma, the insert 24 can have a width of five-sixteenth inch so that when inserted in the slot 46 of a slightly radially expanded inner tube 22, an inner diameter of one quarter inch is achieved for the combination of the inner tube 22 and the insert 24. In addition, inserts having widths different from those specifically mentioned above can be used with an inner tube of the present invention provided that the insert has a width sized not to cause the inner tube to be significantly out of round. In this manner, different sized inserts 24 can be used with a single sized inner tube 22 to achieve a best snug fit of the tracheostomy tube 20 within the stoma 140.

Once the desired size insert 24 is mounted in the slot 46 of the inner tube 22, an appropriately sized outer tube 26 would be selected to accommodate the outer diameter of the combination of inner tube 22 and insert 24. In particular, three outer tubes 26 are preferably provided. Each outer tube has a different diameter sized to accommodate an insert and inner tube combination when one of the respective different width inserts discussed above is mounted in an inner tube.

A preferred embodiment of the tracheostomy tube of the present invention comprises a kit including an inner tube 22, three inserts 24 and three outer tubes 26. Each insert would have a different width and each outer tube would have a different diameter to accommodate a combination of the inner tube and one of the respective different width inserts. The kit may also include a button 28. The kit allows a physician to custom fit a tracheostomy tube of the present invention within a neck of a patient.

Other important dimensions of the tracheostomy tube include the widths of the collar 36 and the flange 76. The collar 36 of the inner tube 22 is preferably 3/32 inch wide, i.e., extends outwardly radially relative to the outer surface 40 of the inner tube 22. The flange 76 of the outer tube 26 is preferably 3/32 inch width, i.e, extends outwardly radially from the outer surface 78 of the outer tube 26. These widths of the collar 36 and the flange 72 are sufficient to anchor the collar 36 and flange 72, respectively, against the anterior wall 130 of the trachea 128.

The tracheostomy tube of the present invention provides several important advantages over prior art tracheostomy tubes. First, the combination of the inner tube 20 and the outer tube 26 yield a tracheostomy tube 20 which has a very low profile, i.e., the proximal end 72 of the outer tube 26 rests substantially flush with the skin surface 124 of the neck 120. Accordingly, when a tracheostomy button 28 is secured over the proximal end 72 of the outer tube 26, the tracheostomy tube 20 becomes hardly noticeable to bypassers and does not attract unwanted attention to the patient. This low profile fit also permits clothes to easily rest over the tracheostomy tube if desired. This low profile can be achieved since the outer tube 26 is secured to the inner tube 22 below the skin surface 124 of the neck 120 instead of being secured to an inner tube outside the skin surface of the neck.

Second, the tracheostomy tube 20 is extremely stable relative to the trachea 128 once fixed relative thereto. This stability facilitates mechanically assisted ventilation because it helps to maintain a good seal between the outer surface 78 of the outer tube 26 and the stoma 140, which in turn permits maintenance of adequate ventilation pressures. The secure attachment of the tracheostomy tube 20 to the trachea 128 is achieved by a combination of the collar 36 and the flange 76 of the outer tube 22, which sandwich the anterior wall 130 of the trachea 128 therebetween. The tracheostomy tube 20 is securely fastened and stable relative to the trachea 128 without the need for accessory fastening devices, such as an elastic band or a cord, which is used in prior art tracheostomy tubes to secure those devices about the neck of a patient. Of course, the lack of an additional securing means, such as a neck band, further contributes to the cosmetic appearance of the tracheostomy tube of the present invention making it less likely to attract unwanted attention from curious observers. The lack of a neck band also makes the tracheostomy tube relatively comfortable.

The tracheostomy tube 20 of the present invention is also particularly convenient to insert and remove relative to the trachea 128. The slot 46 of the inner tube 20 permits radially compression of the inner tube 22 to temporarily reduce the effective outer diameter of the outer surface 40 thereby facilitating insertion and removal of the inner tube 22 through the stoma 140 in the neck 120 of the patient. The slot 46 of the inner tube 22 also allows the use of a plastic material for the inner tube 22 that is harder than the resilient materials of nonconventional prior art tracheostomy tubes because the inner tube 22 does not rely solely on the resilience of the material of the inner tube 22 to reduce its outer diameter for insertion and removal. This harder plastic material increases the stability of the tracheostomy tube 20 when fastened relative to the trachea 128 since the harder plastic remains firm against pressure from the wall of the stoma 140 or the anterior wall 130 of the trachea 128.

More importantly, the slot 46 of the inner tube 22 also allows a single sized inner tube 22 to be adaptable to fit different size stomas 140 within the neck 120 of the patient. The slot design of the inner tube 22 permits a physician to insert the inner tube 22 through the anterior wall 130 of the trachea 128 and then mount different width elongate inserts 24 into the slot 46 of the inner tube 20 to achieve the best fit of the inner tube 22 within the stoma 140 in the neck 120 of the patient. This eliminates guesswork by the physician when choosing the appropriate size tracheostomy tube for insertion within the stoma 140 and trachea 128. In addition, the ability to use a single size inner tube 22 for insertion within the stoma 140 avoids having to stock several different sized inner tube portions of a tracheostomy tube. This cuts down on inventory costs as well as inventory loss when excess tracheostomy tubes must be discarded because they exceed their safe shelf life for sterility purposes.

While many tracheostomy candidates can benefit from the present invention, a tracheostomy tube of the present invention is especially advantageous for patients which need a protected airway at nighttime only. In particular, patients having severe sleep apnea have difficulty breathing through a mouth or nose during certain phases of sleep. One treatment is to install a tracheostomy tube in the neck of a severe sleep apnea patient to permit adequate breathing during sleep. However, the tracheal stoma is not needed for breathing while the patient is awake during daytime hours. Accordingly, the tracheostomy tube can then be covered during the day to allow normal breathing through the nose and mouth and to allow normal function of the vocal cords within the larynx. The tracheostomy tube of the present invention is well suited for this severe sleep apnea patient. The tracheostomy tube can be securely fastened to the neck of a patient for long term use yet is of a low profile preventing unwanted attention to the tracheostomy tube.

The tracheostomy tube 20 of the present invention can also be modified as reflected in the following alternate embodiments. It should be understood that although some features are shown only in alternate embodiments but not others, these features can be incorporated with features from other embodiments in any desired combination.

Figure 9:
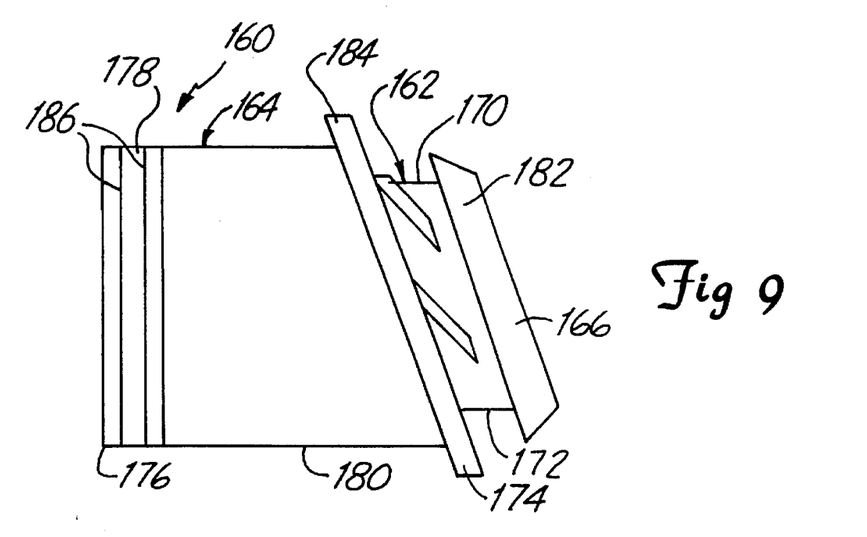
FIG. 9 is a side view in elevation of an alternate embodiment of the tracheostomy tube of the present invention.

As shown in FIG. 9, an alternate embodiment of the present invention includes a tracheostomy tube 160 including an inner tube 162 and an outer tube 164. The inner tube 162 has a distal end 166 and a proximal end (not shown), as well as a top portion 170 and a bottom portion 172. The outer tube 164 has a distal end 174 and a proximal end 176, as well as a top portion 178 and a bottom portion 180. The distal end 166 of the inner tube 162 includes a collar 182 that is beveled from top to bottom and the distal end 174 of the outer tube 164 includes a flange 184 that is beveled from top to bottom. The beveled collar 182 of the inner tube 162 and the beveled flange 184 of the outer tube 164 form an angle relative to a longitudinal axis of the tracheostomy tube 160. The angle preferably ranges from 60 degrees to 85 degrees relative to the longitudinal axis of the tracheostomy tube 160. The beveled collar 182 of the inner tube 162 is achieved by making a length of the top portion 170 of the inner tube 162 shorter than a length of the bottom portion 172 of the inner tube 162. Similarly, the beveled flange 184 of the outer tube 164 is achieved by making a length of the top portion 178 of the outer tube 164 shorter than the length of the bottom portion 180 of the outer tube 164. Although not required, the beveled flange 184 of the outer tube 164 can be made of a material that is relatively resilient. A resilient flange 184 would facilitate secure adaptation of the flange 184 to the anterior wall 130 as well as facilitate sliding rotation of the flange 184 relative to the trachea 128 (when the flange 184 is closely adjacent to the anterior wall 130 of the trachea) while securing the outer tube 164 onto the inner tube 162. Another alternative embodiment could include replacing a resilient flange 184 with an inflatable cuff on the outer surface of the outer tube 164 at its distal end for insuring secure engagement of the outer tube 164 relative to the trachea 128.

Figure 10:
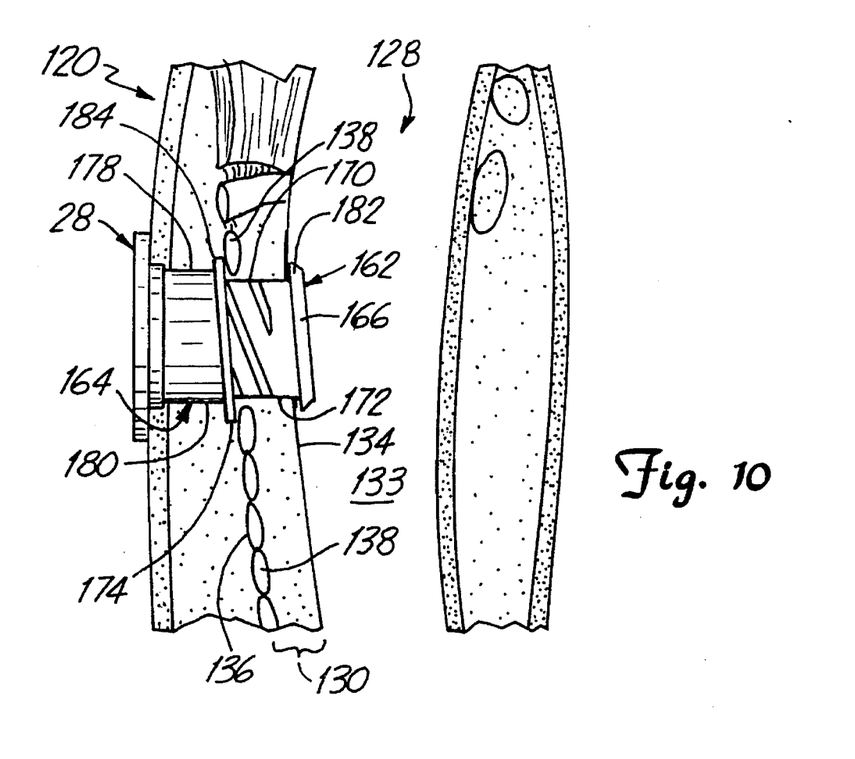
FIG. 10 is a sectional view of the tracheostomy tube of FIG. 9 secured to a trachea within a neck of a patient.

The beveled collar 182 of the inner tube 162 is especially adapted for reciprocally engaging the natural curve of the inner surface 134 of the anterior wall 130. Accordingly, once inserted into the trachea 128 as shown in FIG. 10, the inner tube 162 of the tracheostomy tube 160 can be fastened more securely to the trachea 128 since the proximal end 172 of the inner tube 162 substantially conforms to the natural anatomical configuration of the trachea 128. Similarly, the beveled flange 184 of the outer tube 164 is especially adapted for reciprocally engaging the natural curve of the outer surface 136 of the anterior wall 130 of the trachea 128. As shown in FIG. 10, this results in an outer tube 164 of the tracheostomy tube being more securely fastened to the trachea 128 since the beveled flange 184 substantially conforms to the anatomical configuration of the anterior wall 130.

As shown in FIG. 9, the outer tube 164 can also include a plurality of sizing lines 186 formed in the proximal end 176 of the outer tube 164. These sizing lines 186 define annular ring portions formed in a sidewall of the proximal end of the outer tube 164 and which are prestressed to facilitate cutting through the side wall to shorten the length of the outer tube 164. Alternatively, the annular ring portions can be defined by regions of the outer tube 164 having a reduced wall thickness or having perforated slits. These sizing lines 186, which are visible on an outer surface of the outer tube 164, help the physician to measure and cut the proper length of outer tube 164 needed to obtain a low profile (relative to the skin surface 124) fit of the outer tube 164 within the neck. As discussed later with respect to FIG. 11, similar annular ring portions can be incorporated into the proximal end of the inner tube 162 to facilitate shortening the length of the inner tube 162 for an ideal low profile fit within a tracheal stoma. Although the annular ring portions are discussed with respect to the embodiment of FIG. 9, this feature can be implemented in an outer tube of any of the embodiments of the present invention, including the embodiment of FIG. 1.

Figure 11:
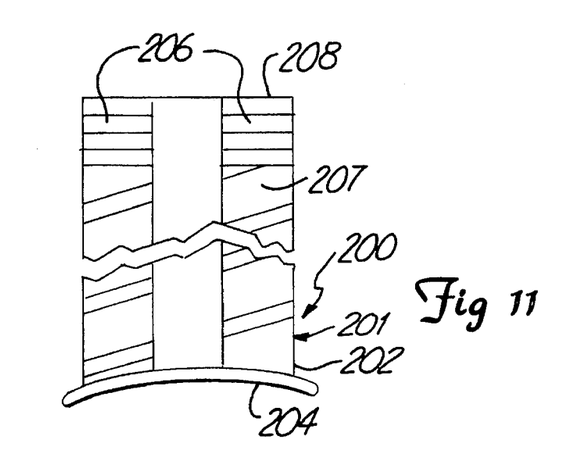
FIG. 11 is a top view in elevation of an alternative embodiment of an inner tube of the tracheostomy tube of the present invention.

Another alternative embodiment of the tracheostomy tube of the present invention is shown in FIG. 11. In this embodiment, a tracheostomy tube 200 includes an inner tube 201 having a distal end 202 with a collar 204. The collar 204 is curved from side-to-side in the shape of a sphere to conform with the natural side-to-side curvature of the anterior wall 130 of the trachea. The curved collar 204 of the inner tube 200 results in a tracheostomy tube 200 which can be fastened more securely to the trachea 128 because the inner tube 201 is adapted and sized to substantially conform to the natural anatomical configuration of the trachea 128.

FIG. 11 also illustrates a plurality of sizing lines 206 formed in a side wall 207 of the inner tube 200 at a proximal end 208 of the inner tube 200. These sizing lines 206 are similar to the sizing lines 186 shown in FIG. 9, i.e., facilitate shortening the length of the inner tube 200 to a desired length. The sizing lines 206 define annular ring portions formed in the side wall 207 of the proximal end 208 of the inner tube 200 and which are prestressed to facilitate cutting through the side wall 207. The annular ring portions can also be defined by regions of the side wall 207 of the inner tube 200 having a reduced wall thickness or having perforated slits. Of course, similar ring portions can be incorporated into an inner tube of any of the embodiments of the present invention.

Figure 12:
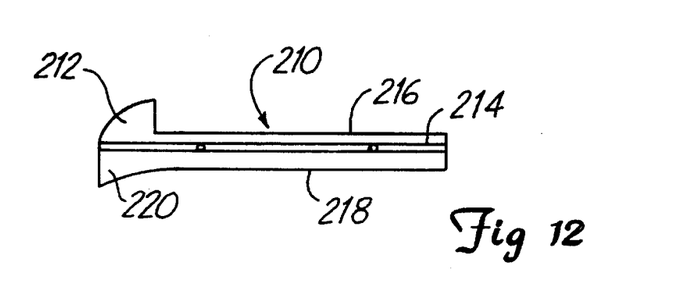
FIG. 12 is a side view in elevation of an alternative embodiment of an elongate insert of the tracheostomy tube of the present invention.
Figure 13:
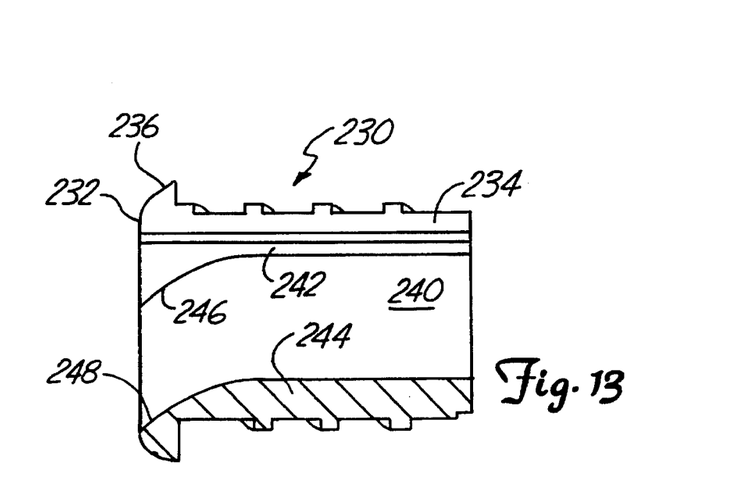
FIG. 13 is a view in section of FIG. 1 as taken along line 13—13 and modified to reflect an alternate embodiment of an inner tube of the present invention.

Another alternative embodiment of the tracheostomy tube of the present invention, is shown in FIGS. 12 and 13. As seen in FIG. 12, an insert 210 includes a distal end 212 and a proximal end 214, as well as an outer surface 216 and an inner surface 218. The insert 210 includes a taper 220 at the distal end 212 on the inner surface 218 formed by increasing the thickness of the insert 210 at the distal end 212 to create a gradual downward curve. As shown in FIG. 13, an inner tube 230 includes a distal end 232 and a proximal end 234 with a collar 236 formed at the distal end 232. The inner tube 230 further includes an outer surface 238 and an inner surface 240, as well as a top portion 242 and a bottom portion 244. An upper taper 246 is formed on the top portion 242 at the distal end 232 and a lower taper 248 is formed on the bottom portion 244 at the distal end 232. The upper taper 246 of the inner tube 230 is sized and adapted to match the taper 220 of the insert 210. Accordingly, the taper 220 of the insert 24, and the upper taper 246 of the inner tube 230 together provide a gentle, gradual downward curve to the upper portion of the distal end of the combination of the inner tube 230 and insert 210 to facilitate insertion and guidance of accessory devices into and through the tracheostomy tube down into the lumen 133 of the trachea 128. This downward taper helps to avoid an accessory device contacting the posterior wall of the trachea 128 directly opposite the distal end of the tracheostomy tube that might occur in the absence of a taper. The lower taper 248 at the distal end 232 of the inner tube 230 complements the upper taper 246 of the inner tube 230 (and the taper 220 of insert 210) to further facilitate guiding accessory devices downward into the lumen 133 of the trachea 128.

Figure 14:
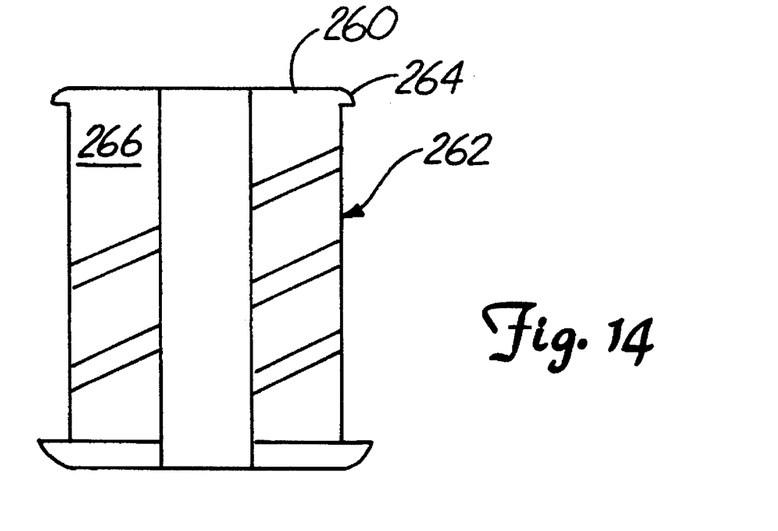
FIG. 14 is a top view in elevation of an alternative embodiment of an inner tube of a tracheostomy tube of the present invention.

As shown in FIG. 14, an inner tube of a tracheostomy tube of the present invention can include other modifications. For example, a proximal end 260 of an inner tube 262 can be formed to include a resilient lip 264 protruding outwardly from an outer surface 266 of the inner tube 262. This lip 264 is sized and adapted to permit sliding movement of an outer tube distally over the proximal end 260 of the inner tube 262. However, once a proximal end of an outer tube passes over the lip 264 of proximal end 260 of the inner tube 262 when being secured thereon, the lip 262 prevents the outer tube from moving proximally relative to the inner tube 262. This arrangement further results in secure attachment of the outer tube relative to the inner tube. Alternatively, or in combination with the inner tube 262, a lip similar to the lip 264 can be incorporated onto a proximal end of an insert of a tracheostomy tube of the present invention for insuring secure attachment of the outer tube relative to the insert when the insert is mounted within an inner tube.

Figure 15:
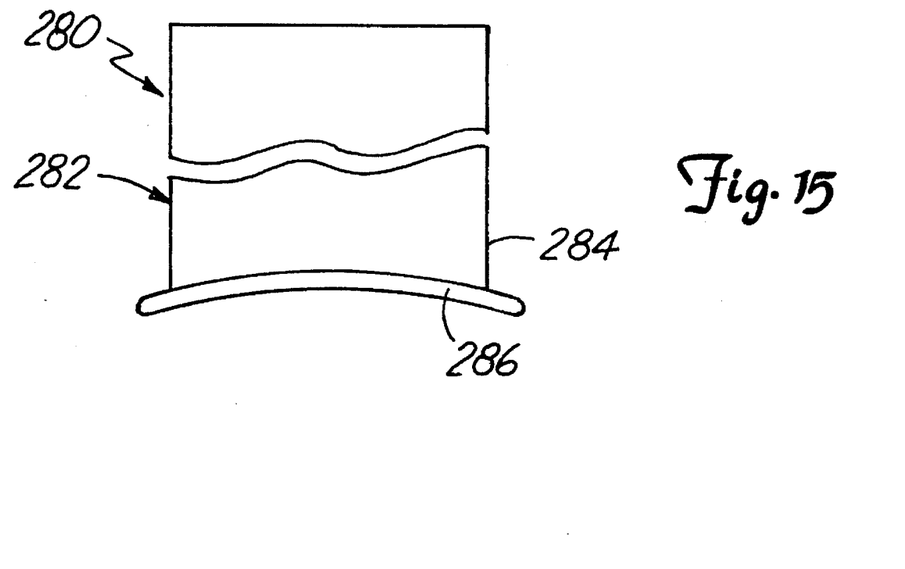
FIG. 15 is a top view in elevation of an alternative embodiment of an outer tube of a tracheostomy tube of the present invention.

FIG. 15 illustrates an alternative embodiment of an outer tube of a tracheostomy tube of the present invention. In this embodiment, a tracheostomy tube 280 includes an outer tube 282 having a distal end 284 with a flange 286. The flange 286 is gradually curved from side-to-side in the shape of a sphere to conform with the natural side-to-side curvature of the anterior wall 130 of the trachea 128. The curved flange 286 of the outer tube 282 results in a tracheostomy tube 280 which can be fastened more securely to the trachea 128 because the outer tube 282 is adapted and sized to substantially conform to the natural anatomical configuration of the trachea 128. The flange 286 can also be made of a relatively resilient material to further accentuate adaptation of the flange 286 relative to the trachea. The resilient flange 286 also facilitates rotation of the flange 286 when closely adjacent to the anterior wall 130 of the trachea to allow the curved flange 286 to slide over the curved surface of the anterior wall. 130 when securing the outer tube 262 onto an inner tube.

The tracheostomy tube of the present invention provides several important advantages over prior art tracheostomy tubes. First, the combination of the inner tube and the outer tube yield a tracheostomy tube which has a very low profile relative to the skin surface of the neck making the tracheostomy tube of the present invention hardly notice, able to bypassers preventing unwanted attention to the patient. Moreover, this low profile fit allows clothes, e.g., a collar, to conveniently fit immediately over the tracheostomy tube, further reducing the likelihood of it being noticed. Second, the tracheostomy tube of the present invention is extremely stable relative to the trachea because the outer tube is secured to the inner tube below the skin surface of the neck and because the inner tube and outer tube sandwich the anterior wall of the trachea. This stability facilitates mechanically assisted ventilation through the tracheostomy tube as well as alleviating the need for an additional securing means such as a neck band around the neck of the patient, which would attract attention to the tracheostomy tube. The lack of a securing neck band provides greater comfort for the wearer. The tracheostomy tube of the present invention is also particularly convenient to insert and remove within the tracheal stoma. The inner tube includes a slot that facilitates radially compressing the inner tube to temporarily reduce its outer diameter during insertion. The slot design of the inner tube also allows a single sized inner tube to be adaptable to fit different sized stomas within the neck of a patient. The insert can be provided with several different sized widths for insertion within the slot of the inner tube to create a combination of the insert and inner tube that snugly fits the tracheal stoma. Several different sized outer tube portions are made available for threadably engaging the "adapted" size of the inner tube and insert combination. In addition, the tracheostomy tube of the present invention can include an inner tube having a beveled collar and an outer tube including a beveled flange, as well as the collar of the inner tube being curved from side-to-side. The combination of these adaptations enables the inner tube and outer tube, respectively, to better conform to the natural anatomical configuration of the anterior wall of the trachea allowing a more secure fastening of the tracheostomy tube to the trachea. In addition, an inner surface of the inner tube and insert can be tapered to facilitate insertion and guidance of accessory devices through the tracheostomy tube of the present invention down into the lumen of the trachea while avoiding direct contact with the posterior wall of the trachea opposite the tracheal stoma.

Although the present invention has been described with reference to preferred embodiments, workers skilled in the art will recognize that changes may be made in form and detail without departing from the spirit and scope of the invention.

What is claimed is:

1. A tracheostomy tube comprising:

an elongate inner tube having a distal end and a proximal end, the inner tube having a side wall with an outer surface having threads formed thereon, the distal end of the inner tube defining an annular collar having an inner diameter substantially equal to an inner diameter of the inner tube and an outer diameter exceeding an outer diameter of the inner tube, and the inner tube having a longitudinal slot extending through the side wall and the collar from the distal end to the proximal end of the inner tube;

an elongate insert slidably mountable in the slot of the inner tube and collar; and an outer tube having an inner surface with grooves formed therein to threadingly engage the threads of the inner tube, the engaged outer tube securing the tracheostomy tube to a neck of a patient.

2. The tracheostomy tube of claim 1 wherein the outer tube further includes an annular flange at a distal end of the outer tube, the flange being curved from side-to-side for reciprocally engaging an outer surface of an anterior wall of the trachea.

3. The tracheostomy tube of claim 1 wherein the insert has an outer surface with threads formed thereon and adapted to be aligned with the threads of the inner tube when the insert is mounted within the slot of the inner tube.

4. The tracheostomy tube of claim 1 wherein the insert has a pair of ridges formed on opposite sides of the insert and the slot of the inner tube is defined by opposed walls, each wall having a groove adapted to receive one of the ridges of the insert for guiding sliding movement of the insert longitudinally relative to the slot and inner tube, the ridges of the insert including protrusions formed thereon and the grooves of the inner tube including recesses formed therein, the protrusions and the recesses being adapted so the protrusions snap fit within the recesses.

5. The tracheostomy tube of claim 1 wherein an inner surface of the inner tube has a taper adjacent its distal end so that a top portion of the inner tube has a wall thickness which increases toward the distal end of the inner tube and so that a bottom portion of the inner tube has a wall thickness which decreases toward the distal end of the inner tube, wherein the inner diameter of the inner surface of the inner tube remains substantially constant and uniform throughout the length of the inner tube from the distal end to the proximal end.

6. The tracheostomy tube of claim 5 wherein the insert has a distal end and a proximal end and an inner surface, the inner surface having a taper of increased wall thickness at the distal end of the insert so that when the insert is mounted within the slot of the inner tube, the taper of the insert aligns with the taper of the inner tube to provide a relatively smooth and constant inner diameter of the inner surface of the inner tube and insert.

7. The tracheostomy tube of claim 1 and further including:
a button for securing over a proximal end of the outer tube, the button having an outer surface and an inner surface which is adapted to lockingly engage the outer tube.

8. The tracheostomy tube of claim 7 wherein an outer surface of the outer tube has a pair of oppositely disposed grooves formed therein, and the button has a pair of oppositely disposed pins formed on an inner surface therein, the grooves of the outer surface of the outer tube and the pins of the button being adapted to reciprocally and lockingly engage each other to releasably fix the button to the outer tube.

9. The tracheostomy tube of claim 1 wherein an end surface of the distal end of the inner tube is curved from side-to-side for reciprocally engaging an inner surface of an anterior wall of the trachea.

10. The tracheostomy tube of claim 1 wherein an end surface of the distal end of the inner tube is beveled relative to a longitudinal axis of the inner tube.

11. The tracheostomy tube of claim 1 wherein an end surface of the distal end of the outer tube is beveled relative to a longitudinal axis of the outer tube.

12. The tracheostomy tube of claim 1 wherein a side wall of the outer tube has at least one annular ring portion adjacent its proximal end which is prestressed to facilitate cutting through the ring portion of the side wall to shorten the length of the outer tube.

13. The tracheostomy tube of claim 1 wherein the side wall of the inner tube has an annular ring portion formed therein which is prestressed to facilitate cutting through the ring portion of the side wall to shorten the length of the outer tube.

14. A method of securing a tracheostomy tube to a neck of a patient, the neck having a hole formed therein extending from the outer surface of the neck through an anterior wall of a trachea within the neck, the hole having a first diameter, the method comprising:
providing an elongate inner tube having a distal end and a proximal end, the inner tube having a side wall with an outer surface having threads formed thereon, the distal end of the inner tube defining an annular collar having an inner diameter substantially equal to an inner diameter of the inner tube and an outer diameter exceeding an outer diameter of the inner tube, the inner tube having a longitudinal slot extending through the side wall and the collar from the distal end to the proximal end of the inner tube;
squeezing the inner tube so that the outer diameter of the inner tube is reduced to a diameter which is less than the diameter of the hole in the neck;
orienting the inner tube so that the annular collar of the inner tube is aligned to enter the hole in the neck and advancing the inner tube while still squeezing the inner tube so that the collar passes through the hole and into the lumen of the trachea;
positioning the inner tube so that the collar of the inner tube seats firmly against the inner surface of the anterior wall of the trachea and the proximal end of the inner tube extends outwardly beyond the outer surface of the neck;
releasing the inner tube so that it returns to its original outer diameter;
sliding an elongate insert into the slot of the inner tube to cause the side wall of the inner tube and insert to be continuous about its periphery;
providing an outer tube having an inner surface with grooves formed thereon adapted to threadingly engage the threads of the inner tube, and the outer tube having a flange formed at a distal end of the outer tube;
advancing the outer tube over the inner tube with the grooves of the outer tube engaging the threads of the inner tube, the outer tube being advanced relative to the inner tube until the flange of the outer tube seats against the outer surface of the anterior wall of the trachea within the neck to secure the tube onto the neck of a patient.

15. A method of securing a tracheostomy tube to a neck of a patient, the neck having a stoma formed therein extending from the outer surface of the neck through an anterior wall of a trachea within the neck, the method comprising:
inserting an elongate inner tube through the stoma so that a collar at a distal end of the inner tube rests against an inner surface of the anterior wall of the trachea and a proximal end of the inner tube is adjacent the exterior surface of the neck, the inner tube having a side wall with a longitudinal slot extending through the side wall from the distal end to the proximal end of the inner tube to facilitate insertion of the inner tube;
mounting an elongate insert in the slot of the inner tube; and
securing an outer tube onto the inner tube and insert so that a flange of at a distal end of the outer tube presses against an outer surface of the anterior wall of trachea and the collar of the inner tube presses against the inner surface of the anterior wall of the trachea to secure the tracheostomy tube to a neck of a patient.

16. The method of claim 15 wherein the step of inserting further includes:
providing the inner tube with grooves formed in the edges of the side wall defining the slot, each groove including a pair of recesses formed therein.

17. The method of claim 16 wherein the step of mounting further includes:
providing the insert with a pair of ridges on opposite sides of the insert, the ridges extending along the length of the insert and being adapted for reciprocally engaging the grooves of the slot in the inner tube to permit sliding movement of the insert longitudinally relative to the inner tube, the ridges further including at least one pair of knobs formed thereon on opposite sides of the insert and adapted for snap fitting within the recesses of the grooves of the slot to lock the insert within the slot.

18. The method of claim 17 wherein the step of securing further includes the inner tube having an outer surface with threads formed thereon and the outer tube having an inner surface with grooves formed thereon, the grooves of the outer tube being sized and aligned to threadingly engage the threads of the inner tube to permit longitudinal movement of the outer tube relative to the inner tube and to provide positive engagement between the inner tube and outer tube to secure the inner and outer tubes relative to one another.

19. A tracheostomy tube comprising:

an elongate tubular member having a distal end and a proximal end, the tubular member having a circumferential wall defined by an inner surface and an outer surface, the inner surface and the outer surface having an inner diameter and an outer diameter, respectively, the outer surface having threads formed thereon, and the tubular member having a longitudinal slot through the wall extending from the distal end to the proximal end;

an annular collar having a distal end and a proximal end, the proximal end of the collar being attached to the distal end of the tubular member, the collar having an inner diameter substantially equal to the inner diameter of the tubular member, and an outer diameter exceeding the outer diameter of the tubular member, the collar having a slot extending from the distal end to the proximal end, the slot in the collar aligned with the slot in the tubular member;

a elongate insert slidably mountable in the slot of the collar and the tubular member;

a tubular sleeve having an inner surface with grooves formed thereon to threadingly engage the threads of the tubular member, the engaged tubular sleeve securing the tracheostomy tube to a neck of a patient.

20. A tracheostomy tube comprising:

an elongate inner tubular member having a distal end and a proximal end, the tubular member having a circumferential wall defined by an inner surface and an outer surface, the inner surface and the outer surface having an inner diameter and an outer diameter, respectively, the outer surface having threads formed thereon, and the tubular member having a longitudinal slot through the wall extending from the distal end to the proximal end, the slot being defined by edges of the side wall and each edge of the side wall having a groove formed therein, and the inner surface of the inner tube being tapered such that the inner surface at the distal end of the inner tube is angled downward along a smooth curve relative to a longitudinal axis of the inner tube and the top portion of the inner tube;

an annular collar having a distal end and a proximal end, the proximal end of the collar being attached to the distal end of the inner tubular member, the collar having an inner diameter substantially equal to the inner diameter of the inner tubular member, and an outer diameter exceeding the outer diameter of the inner tubular member, the collar having a slot extending from the distal end to the proximal end, the slot in the collar aligned with the slot in the tubular member, the collar being curved from side-to-side and beveled from top-to-bottom to reciprocally engage an inner surface of the anterior wall of the trachea;

a elongate insert slidably mountable in the slot of the collar and the inner tubular member, the insert having a pair of ridges having a pair of oppositely disposed ridges formed on the sides of the insert and adapted for reciprocally engaging the grooves of the slot; and an elongate outer tubular sleeve having an inner surface with grooves formed therein to threadingly engage the threads of the inner tubular member and having a flange formed at a distal end of the outer tube, the flange being curved from side-to-side and beveled from top-to-bottom to reciprocally engage an outer surface of the anterior wall of the trachea.

* * * * *